United States Patent
Klaver et al.

(10) Patent No.: US 11,058,090 B2
(45) Date of Patent: Jul. 13, 2021

(54) HYBRID TRUE POTATO SEED OF TETRAPLOID HYBRID 1490185

(71) Applicant: Bejo Zaden B.V., Warmenhuizen (NL)

(72) Inventors: Martinus Jacobus Theodorus Klaver, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 28 days.

(21) Appl. No.: 16/320,216

(22) PCT Filed: Jul. 25, 2016

(86) PCT No.: PCT/EP2016/067656
§ 371 (c)(1),
(2) Date: Jan. 24, 2019

(87) PCT Pub. No.: WO2018/019359
PCT Pub. Date: Feb. 1, 2018

(65) Prior Publication Data
US 2019/0269095 A1    Sep. 5, 2019

(51) Int. Cl.
*A01H 6/82* (2018.01)
*A01H 5/06* (2018.01)
*A01H 5/10* (2018.01)
*A01H 5/04* (2018.01)

(52) U.S. Cl.
CPC .............. *A01H 6/827* (2018.05); *A01H 5/04* (2013.01); *A01H 5/06* (2013.01); *A01H 5/10* (2013.01)

(58) Field of Classification Search
None
See application file for complete search history.

(56) References Cited

U.S. PATENT DOCUMENTS 6,297,194 B1 * 10/2001 Miller .................... A01N 57/24
                                                        504/197
8,330,004 B2 * 12/2012 Hoopes ................... A01H 5/04
                                                        800/317.2

FOREIGN PATENT DOCUMENTS

WO    2011053135 A2    5/2011

OTHER PUBLICATIONS

Macaso-Khwaja et al. Philippines Journal of Crop Science 11(2): 89-96 (1986).*
Kidane-Mariam et al., "Performances of True Potato Seed Families Derived From Intermating Tetraploid Parental Lines", American Potato Journal, 1985, pp. 643-652, vol. 62.
Ortiz, "Ploidy manipulation of the gametophyte, endosperm and sporophyte in nature and for crop improvement: a tribute to Professor Stanley J. Peloquin (1921-2008)", Annals of Botany, 2009, pp. 795-807, vol. 104.
Simmonds, "A review of potato propagation by means of seed, as distinct from clonal propagation by tubers", Potato Research, 1997, pp. 191-214, vol. 40.

* cited by examiner

*Primary Examiner* — Cathy Kingdon Worley
(74) *Attorney, Agent, or Firm* — The Webb Law Firm

(57) ABSTRACT

Provided herein are hybrid True Potato Seeds (TPS). Also provided herein are potato plants grown from the present hybrid True Potato Seeds and the potato tubers produced by these plants. Also provided herein is use of the present potato tubers for vegetative propagation thereof and to the use of the present potato tubers as seed potato for producing potato tubers for consumption and the food processing industry. Specifically, provided herein are hybrid True Potato Seed (TPS), wherein the seed is tetraploid and is produced as an F1 of a cross between a tetraploid male potato line and a tetraploid female potato line and preferably to hybrid True Potato Seed (TPS) wherein said tetraploid male potato line and said tetraploid female potato line have a sufficient degree of genetic and phenotypic uniformity to yield, as F1, hybrid True Potato Seed (TPS).

5 Claims, 1 Drawing Sheet

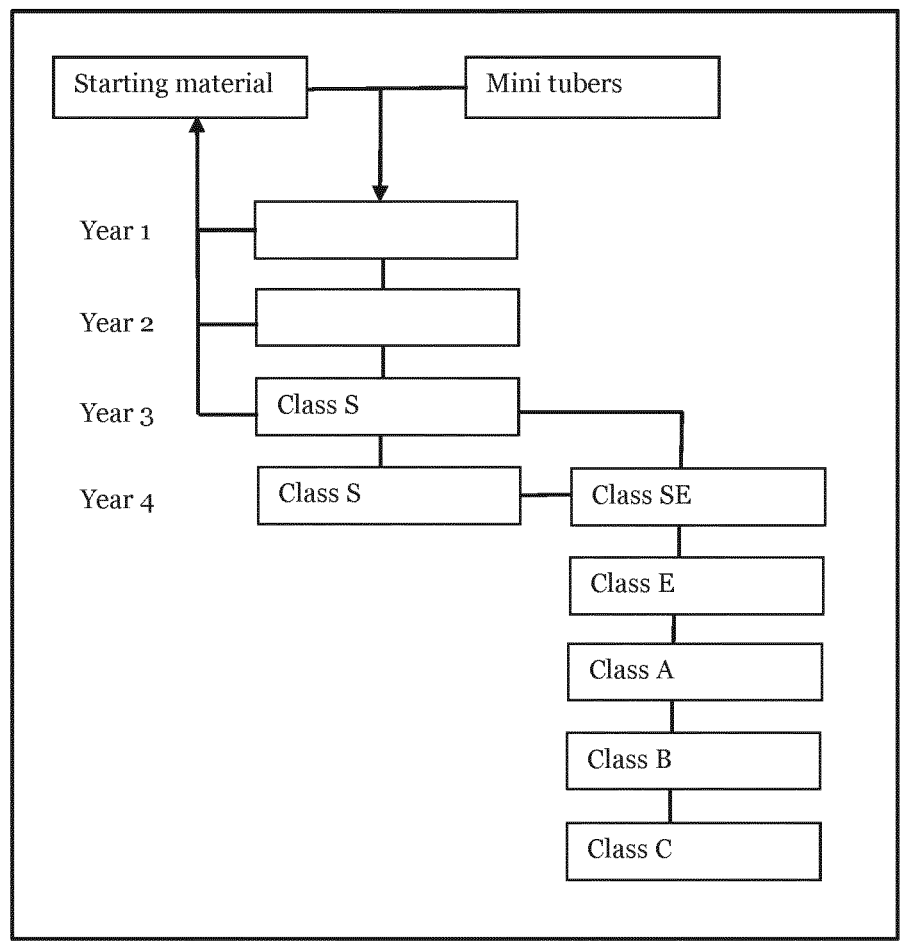

HYBRID TRUE POTATO SEED OF TETRAPLOID HYBRID 1490185

CROSS-REFERENCE TO RELATED APPLICATION

This application is the United States national phase of International Application No. PCT/EP2016/067656 filed Jul. 25, 2016, the disclosure of which is hereby incorporated by reference in its entirety.

The present invention relates to hybrid true potato seeds or TPS. The present invention further relates to potato plants grown from the present hybrid true potato seeds and the potato tubers produced by these plants. The present invention also relates to the use of the present potato tubers for vegetative propagation thereof and to the use of the present potato tubers as seed potato for producing potato tubers for consumption and the food processing industry and for industrial applications.

Potato, or *Solanum tuberosum* L., is traditionally sold as a vegetatively propagated tuber crop. For vegetative propagation of potato, use is made of potato tubers commonly designated as seed potatoes however the term "seed potatoes" must not be confused with the generally accepted term "true potato seed" or TPS for botanical seeds of potato.

The potato tubers are thickened rhizomes or stolons. After planting, this tuber produces one or more shoots that each grows into a stem and leaves. The mature plant forms new tubers which are harvested at the end of the growing season and which genetically can be regarded as clones of the mother plant. Used as food, a potato tuber is rich in carbohydrates, protein, fiber, vitamin B and C and minerals as iron, zinc and magnesium. Potatoes are consumed cooked, fried (as chips), as mashed potatoes, as salad, crisps or chips and so forth; further, potatoes are also grown as seed potatoes (to be used for further vegetative production) and as source of starch having numerous industrial applications.

The development of a new clonal variety of potato is a time consuming process; this development is based on crossing two existing varieties, harvest the seeds and select, from the progeny obtained, the most suitable clone for the objective of the breeding effort. After this crossing and selection stage a long period of year by year vegetative propagation of the clone is necessary to produce a reasonable amount of seed potatoes, thus not seeds but tubers. To plant one hectare for potato production, about 2,500 kg of seed potatoes (tubers) are required.

The year by year vegetative propagation of seed potatoes also results in a risk that the crop becomes infected with nematodes, viroids and viral, bacterial or fungal diseases. In general, with every year of vegetative propagation, the amount of pathogens increases. To ensure that seed potatoes are free of disease, in the EU, but also in other countries, there is a schedule of classification to minimize the risk of spreading these diseases. The EU directive 2014/20 describes grades of the basic and certified seed potatoes depending of the number of field generations of vegetative multiplication. Decisive here is the number of field generations, i.e. with each field generation the tubers are shifted to a lower class. The highest quality level, S, must be derived from a selected plant (nuclear stock), tissue culture material or from minitubers. Classes S, SE and E (basic category) are for further propagation of seed potatoes; the certified categories A and B are meant for production of consumption or table potatoes in the broadest sense of the word. Every produced lot of potatoes is assigned a class; according to this schedule it is allowed to be put on the market (see also FIG. 1).

Potatoes are, until now, vegetatively propagated by multiplying tubers in successive cycles; per cycle an average multiplication of about a factor 10 is achieved. The propagation material used, however, is placed in a lower class after every field generation concerning the health of the material. Therefore, propagation is limited by the permission to use the tubers for further seed material or that they are classified as product for the consumption market only. The rationale for this is, that with every cycle of propagation the tubers produced can be infected by fungi, bacteria, nematodes and/or viruses. Additionally, with every cycle the material is subjected to tests for determining the plant health and using this result a class is determined. The process of vegetative propagation is, next to time consuming, very expensive and labour-intensive; it is difficult to produce healthy potato propagation material which is free or almost free of tuber transmissible diseases and pests.

Considering the above, it is desirable to develop a method to efficiently supply basic potato material which is free of accumulated tuber borne pathogens as viroids, viruses, bacteria and fungi.

Hybrid potato seeds, thus not potato tubers, are generally produced by applying pollen of a male, or pollinator plant, to pollinate a female line. Both tetraploid parent lines are homozygous to a certain degree and are specifically selected for a sufficient degree of genetic and phenotypic uniformity. These parental, or inbred, lines for tetraploid hybrid seed production are propagated vegetatively to ensure their genetic stability.
Using these selected tetraploid parents results in a sufficient uniform hybrid offspring which has an high value on the market.

Diploid potato has so called gametophytic incompatibility meaning that there is an interaction between the SI allele present in pollen and both SI alleles present in the stigma. When the pollen grain has an allele identical to at least one of the alleles in the stigma, germination of the pollen grain on the stigma is prevented. Germination of pollen is only possible on a stigma with other SI alleles then present in this pollen. The S locus harbouring the allele, is very polymorph, meaning that there is a large number of different SI alleles. This SI system in diploid potato prevents self-pollination but also prevents the development of genetically uniform parent lines by inbreeding.

In order to develop potato material with sufficient homozygosity, or uniformity, several companies are performing research on diploid potato material in order to develop suitable starting material. One example of this research is described in patent application WO2011053135. Central to the disclosure in this application is breeding of potato (*S. tuberosum* L.) on the diploid level. Problem with breeding on this ploidy level with potato is the occurring of self-incompatibility which prohibits the necessary self-fertilization. In these diploid potato plants, self-pollination however is possible when next to the SI alleles, preventing self-pollination, another genetic determinant, Sli (S locus inhibitor), is present. This Sli gene is introgressed from a diploid wild potato accession, *S. chacoense*. The Sli gene counteracts the interaction of identical SI alleles in pollen and stigma, thus enabling self-pollination of the plant. By introducing this gene in diploid *S. tuberosum* it became possible to develop pure inbred lines by repeated self-fertilization. However, it can be envisaged that yield of a diploid crop is lower than that from its tetraploid counterpart so there is a yield penalty when using this approach. This drawback can be overcome by doubling the chromosome number; however there are risks of introducing mutations or aberrant chromosome numbers by this technique.

It is an object of the present invention, amongst other objects to obviate at least some of the above problems associated with production of potatoes either as seed potatoes, consumption potatoes (table potatoes), for the food processing industry or potatoes for industrial processing.

This object, amongst other objects, is met by the present invention as outlined in the appended claims.

Specifically, this object, amongst other objects, is met according to the present invention by providing hybrid True Potato Seed (TPS), wherein said seed is tetraploid and produced as an F1 of a cross between a tetraploid male potato line and a tetraploid female potato line.

The present inventors succeeded in developing suitable material serving as parental lines for the present hybrid seeds which can be marketed as True Potato Seed or TPS. After investing many years in research, the present inventors succeeded to develop parental lines from tetraploid material which can be used to produce hybrid varieties of sufficient uniformity in sufficient commercial quantities.

Parental lines with sufficient genetic and phenotypic uniformity to be used for the tetraploid hybrid seed production are propagated vegetatively.

The present hybrid potato seeds offer several advantages over the application of seed potatoes for cultivation of tubers as seed potatoes, for direct consumption, for the food processing industry or for industrial processing:
- The amount of starting material necessary for 1 ha of potato plants is reduced from 2,500 kg of seed potatoes or tubers to about 80-100 grams of TPS for direct drilling or by using transplants grown from this amount of true potato seeds
- Producing (grams of) seeds rather than (tons of) tubers saves both strongly financially (storage, transport) as well as on natural resources
- The seeds supplied for cultivation are harvested from plants grown under controlled conditions; compared to tubers which have been propagated for 6 or more seasons, this starting material can be considered essentially free of pests and diseases
- Due to this character, the application of labour and chemicals can be strongly reduced.

The present invention preferably relates to hybrid True Potato Seed (TPS) wherein the tetraploid male potato line and the tetraploid female potato line have a sufficient degree of genetic and phenotypic uniformity to yield, as F1, hybrid True Potato Seed (TPS).

The present hybrid seeds are substantially, or completely, free of the common pathogens which may be present in clonal propagated seed potatoes. Due to this fact a large saving can be reached since less chemical treatments of starting material and the field are necessary; this is both a financial as an environmental benefit.

Further, in contrast to the 2,500 kg of seed potatoes needed for planting 1 hectare, using the present hybrid seeds, an amount of about 80-100 gram is sufficient for this hectare, either by direct drilling or by using transplants grown from this amount of seeds.

The present hybrid seeds are produced by pollination of a suitable female or mother line by pollen of a pollinator or father line. Both parental lines, the male and the female line, have to be highly uniform in order to yield an uniform hybrid. Suitable lines which can be used as female lines can be:

- Lines that are self-incompatible
- Lines that are self-compatible and are emasculated
- Lines that produce non-viable pollen
- Cytoplasmic male sterile (thus female) lines
- Genetic male sterile plants Thus, the present invention, according to another preferred embodiment relates to hybrid True Potato Seed (TPS), wherein the tetraploid female potato line has a phenotype selected from the group consisting of self-incompatible tetraploid plants.

According to yet another preferred embodiment, the present tetraploid hybrid True Potato Seed (TPS) produces plants not capable of producing seed bearing berries. An advantageous embodiment for producing the present hybrid seed is also that the mother- or female line can produce hybrid seed after cross pollination with another genotype while self-pollination of the female flowers is prevented by self-incompatibility. In case of TPS producing lines it is a need that the female line must be able to produce seed berries after cross pollination with another genotype but it is an advantage that the resulting hybrid offspring does not produce berries.

After cultivation of potatoes, emergence of volunteers from tubers, accidentally left in the field, is common and these plants emerge in the following season, in general these are removed by spraying with a suitable herbicide.

However, volunteers growing from seeds, which in turn originate from seed bearing berries, can emerge several years later so are difficult to combat and also are a "reservoir" to maintain soil-borne diseases. Because of not producing berries this undesirable regrowth of volunteers from seed is prevented when applying material developed in the described invention.

In another embodiment of the invention, a tetraploid potato line which can be used as female line is manually emasculated and successively hand pollinated by pollen from a suitable tetraploid male potato plant.

In another embodiment of the invention, hybrid seed is produced by hand pollination of the self-incompatible female tetraploid plant with pollen from the male potato plant.

In yet another embodiment, flowers to be pollinated are opened in a juvenile stage to apply pollen on the already receptive stamen.

In one embodiment of the invention, pollination of the self-incompatible female plant, the emasculated compatible plant, the plant which produces non-viable pollen, the genetic male sterile plant or the CMS plant is performed by insects as bees (*Apis mellifera*), bumble-bees (*Bombus* spp.) or blowflies, e.g. *Calliphora* and *Lucilia* spp. In one embodiment of the invention, pollination of the self-incompatible female plant, the emasculated compatible plant, the plant which produces non-viable pollen, the genetic male sterile plant or the CMS plant is performed by mechanical means designed to disperse pollen on plants or receptive flowers.

According to an especially preferred embodiment, the present invention relates to hybrid True Potato Seed (TPS) whereof a representative sample is deposited under NCIMB 42469 (NCIMB National Collections of Industrial, Food and Marine Bacteria (NCIMB), NCIMB Limited, Ferguson Building; Craibstone Estate, Bucksburn ABERDEEN, Scotland, AB21 9YA United Kingdom) on Oct. 23, 2015.

A description of this potato is made using the classical Technical Questionnaire as provided by UPOV (http://www.upov.int/edocs/tgdocs/en/tg023.pdf) dated Dec. 1, 2005. It should be taken in consideration this Questionnaire is devised for clonal propagated material; this seed propagated hybrid cannot be as uniform as a clone will be.
Using this Questionnaire as a guideline the tetraploid potato hybrid 1490185 is described as follows:

| CPVO # | Characteristic | Class |
|---|---|---|
| 1 | Lightsprout size | Medium |
| 2 | Lightsprout shape | Spherical-ovoid |
| 3 | Lightsprout intensity of anthocyanin coloration at base | Medium |
| 4 | Lightsprout: proportion of blue in anthocyanin coloration of base | Medium to high |
| 5 | Lightsprout: pubescence of base | Weak |
| 6 | Lightsprout: size of tip in relation to base | Small-medium |
| 7 | Lightsprout: habit of tip | Closed |
| 8 | Lightsprout: anthocyanin coloration of tip | Very weak |
| 9 | Lightsprout: pubescence of tip | Weak |
| 10 | Lightsprout: number of root tips | Very few to few |
| 11 | Lightsprout: length of lateral shoots | Short |
| 12 | Plant: foliage structure | Intermediate |
| 13 | Plant: growth habit | Semi upright |
| 14 | Stem: anthocyanin coloration | Absent/very weak |
| 15 | Leaf: outline size | Small to medium |
| 16 | Leaf: openness | Intermediate |
| 17 | Leaf: presence of secondary leaflets | Medium |
| 18 | Leaf: green colour | Dark |
| 19 | Leaf: anthocyanin coloration on midrib of upper side | Absent or very weak |
| 20 | Second pair of lateral leaflets: width in relation to length | Medium |
| 21 | Terminal and lateral leaflets: frequency of coalescence | Absent or very low |
| 22 | Flower bud: anthocyanin coloration | Absent to weak |
| 23 | Plant: height | Medium |
| 24 | Plant: frequency of flowers | Very high |
| 25 | Inflorescence: size | Medium |
| 26 | Inflorescence: anthocyanin coloration on peduncle | Absent to weak |
| 27 | Flower corolla: size | Medium |
| 28 | Flower corolla: intensity of anthocyanin coloration on inner side | Absent or very weak |
| 29 | Flower corolla: proportion of blue in anthocyanin coloration on inner side | Absent or low |
| 30 | Flower corolla: extent of anthocyanin coloration on inner side | Absent to very small |
| 31 | Plant: time of maturity | Late |
| 32 | Tuber: shape | Oval |
| 33 | Tuber: depth of eyes | Shallow |
| 34 | Tuber: colour of skin | Yellow |
| 35 | Tuber: colour of base of eye | Yellow |
| 36 | Tuber: colour of flesh | Light yellow |
| 37 | Light beige and yellow skinned varieties only: Tuber: anthocyanin coloration of skin in reaction to light | Weak |

When the product, commercially applicable true potato seed, is available, this opens up the application of several seed-technological treatments which further add unique characters to the crop potato or *Solanum tuberosum*.

Seeds, in general, can be germinating late due to a mechanism called dormancy. This biological mechanism in nature prevents seeds of germination too early in a season; after a prolonged period of cold seeds are ready to germinate. In this way the emerged plantlets have no or a reduced risk of freezing. For plant growers however, dormancy is a process which also prevents timely germination when sowing seeds short after harvesting. Several treatments were developed in the past to break dormancy, among these are:

Scarification, the deliberate damaging of the seed hull so it permits transfer water and air to the embryo;

Stratification, keeping the seeds (eventually in soil) at low temperatures, thereby in fact mimicking winter.

Priming, the pre-germination of seeds until the point they are about to germinate. This results in an early and very uniform germination of the primed seeds; also a dormancy breaking effect is provided by this treatment. Also, because of the rapid emergence of the crop, the need for combatting weeds is lower since the crop grown very early covers the soil sufficiently to prevent weeds from competing with the desired crop. Further priming enables cultivation of a crop in areas with a short growing season.

Modern sowing equipment requires a round and smooth shape of seeds to ensure good sowing results. Since many seeds do not meet this requirement, techniques are developed to provide seeds with a layer of material (e.g. clay) which provide the desired shape and smoothness of the seed and also contribute to the weight of it. Seed treatments as encrusting (adding just enough material to cover irregularities in the seed skin) and pelleting (in addition, giving the seed an uniform round shape and a desired size) are enabled.

Adding this material to the surface of the seed also opens up the opportunity to add compounds to the coating as fungicides, benificials as advantageous microbes, micronutrients but also a characteristic as a specific colour by which seeds of a company are recognized in the market. This added colour also helps the farmer in checking afterwards whether seeds were sown singular and in a regular manner. More to that, also addition of germination promoting compounds as plant hormones is possible.

All these techniques together with the unique characteristics of the sufficiently uniform tetraploid hybrid potato seeds enable a complete new and competitive way of growing potato tubers.

Within the context of the present invention, coating can be defined as a relatively thin layer of polymer supplied to the seed; to this polymer fungicides or insecticides can be added to protect the seed against soil borne pathogens and insect damage. Additionally, a dye can be added, giving the opportunity to check for correct drilling of the seeds. Alternatively, also other beneficial compound scan be added as micronutrients or beneficial micro-organisms promoting the growth of the young seedlings. Encrusted seeds are not only are covered with a polymer with or without extra substances as described above but also the seeds are provided with a smooth surface. This makes drilling easier and the added weight enables a more precise direct drilling of seeds treated this way. With pelleting the seeds are covered with more material, e.g. polymer bound clay, to produce a regularly shaped, round pellet. This pellet, besides eventually having the protecting substances described above, can be constructed in such a way that it will melt or split after water uptake. Priming: priming or pre-germination is a treatment where seeds are given enough moisture to have a onset of germination of the embryo inside the seed. This results in a faster emergence of the seedling, a higher emergence rate and better growth. It is believed that this head-start results in a good root system going down the soil early and grows faster.

Considering the beneficial properties of the present tetraploid hybrid potato seeds, the present invention also relates to potato plants grown from the present hybrid True Potato Seed (TPS) and to potato tubers from such potato plant.

The present invention further relates to the use of the present potato tubers for vegetative propagation thereof and the use of the present hybrid True Potato Seed (TPS) for the production of potato tubers for use as seed potatoes, consumption as table potatoes, the food processing industry and for industrial applications.

In another embodiment of the invention, first generation tubers (from seed) can be used as seed potato of a high certified category.

In another embodiment smaller tubers from this first year material from seed, unsuitable to be used as seed potato, can be applied for a further year of cultivation to produce seed potatoes, still as a high class of certified material according to the schedule in FIG. 1 on page 9.

In another embodiment first generation tubers (from seed) can be used as consumption potatoes, for the food processing industry of for other industrial applications, while smaller tubers are used for a second year of propagation, still as a high class of certified material according to the schedule of FIG. 1.

This makes drilling easier and the added weight enables a more precise direct drilling of seeds treated this way. With pelleting the seeds are covered with more material, e.g. polymer bound clay, to produce a regularly shaped, round pellet. This pellet, besides eventually having the protecting substances described above, can be constructed in such a way that it will melt or split after water uptake. Priming: priming or pre-germination is a treatment were seeds are given enough moisture to have a onset of germination of the embryo inside the seed. This results in a faster emergence of the seedling, a higher emergence rate and better growth. It is believed that this head-start results in a good root system going down the soil early and grow faster.

Considering the beneficial properties of the present tetraploid hybrid potato seeds, the present invention also relates to potato plants grown from the present hybrid True Potato Seed (TPS) and to potato tubers from such potato plant.

The present invention further relates to the use of the present potato tubers for vegetative propagation thereof and the use of the present hybrid True Potato Seed (TPS) for the production of potato tubers for use as seed potatoes, consumption as table potatoes, the food processing industry and for industrial applications.

In another embodiment of the invention, first generation tubers (from seed) can be used as seed potato of a high certified category.

In another embodiment smaller tubers from this first year material from seed, unsuitable to be used a seed potato, can be applied for a further year of cultivation to produce seed potatoes, still as a high class of certified material according to the schedule in FIG. 1 on page 9.

In another embodiment first generation tubers (from seed) can be used as consumption potatoes, for the food processing industry of for other industrial applications, while smaller tubers are used for a second year of propagation, still as a high class of certified material according to the schedule of FIG. 1.

The invention claimed is:

1. A True Potato Seed (TPS) of tetraploid hybrid 1490185, wherein said hybrid was produced as an F1 of a cross between a tetraploid male potato line and a tetraploid female potato line, wherein a representative sample of said hybrid seed is deposited under NCIMB 42469.

2. The hybrid True Potato Seed (TPS) according to claim 1, wherein said seed is coated, encrusted, pelleted, or primed.

3. A potato plant grown from a hybrid True Potato Seed (TPS) according to claim 1.

4. A potato tuber from a potato plant according to claim 3.

5. A method of producing a potato plant, comprising vegetatively propagating the potato tuber according to claim 4.

* * * * *